United States Patent [19]

Sohn et al.

[11] Patent Number: 5,142,075
[45] Date of Patent: Aug. 25, 1992

[54] ANTI-TUMOR PLATINUM(II) COMPLEXES AND PROCESS FOR THE PREPARATION THEREOF

[75] Inventors: Youn S. Sohn; Kwan M. Kim, both of Seoul, Rep. of Korea

[73] Assignee: Korea Institute of Science and Technology, Seoul, Rep. of Korea

[21] Appl. No.: 797,125

[22] Filed: Nov. 22, 1991

[30] Foreign Application Priority Data

Jul. 5, 1991 [KR] Rep. of Korea ............... 11401

[51] Int. Cl.$^5$ .............................................. C07F 15/00
[52] U.S. Cl. .................................................. 556/137
[58] Field of Search ................................ 556/136, 137

[56] References Cited

U.S. PATENT DOCUMENTS

| | | | |
|---|---|---|---|
| 4,533,502 | 8/1985 | Rochon et al. | 556/137 X |
| 4,560,782 | 12/1985 | Papageorgion et al. | 556/137 |
| 4,565,884 | 1/1986 | Andrulis, Jr. et al. | 556/137 |
| 4,730,069 | 3/1988 | Kolar et al. | 556/137 |
| 4,797,393 | 1/1989 | Farrell et al. | 556/137 X |

Primary Examiner—Arthur C. Prescott
Attorney, Agent, or Firm—Scully, Scott, Murphy & Presser

[57] ABSTRACT

The present invention relates to anti-tumor platinum complexes represented by the general formula I:

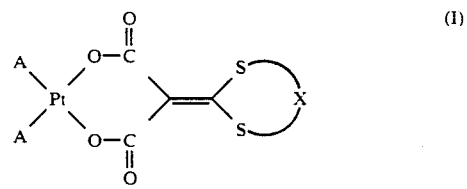

wherein A is selected from the group consisting of ammine and mondentate primary alkyl- and cycloalkylamines having 1-3 carbon atoms such as methyl, ethyl, n-propyl-, isopropyl- and cyclopropylamines, or the two amine groups may be combined to be a bidentate diamine of the chelating form AA such as ethylenediamine, 1,2-diaminocyclohexane, and 2-hydroxy-1,3-diaminopropane, and X is either vinylene(—CH=CH—) or ethylene (—CH$_2$—CH$_2$—) when it is bound to two sulfur atoms in a cyclic form or represents two methyl groups separately bound to each sulfur atom.

4 Claims, No Drawings

ANTI-TUMOR PLATINUM(II) COMPLEXES AND PROCESS FOR THE PREPARATION THEREOF

SUMMARY OF THE INVENTION

The present invention relates to anti-tumor platinum coordination compounds represented by the following general formula I

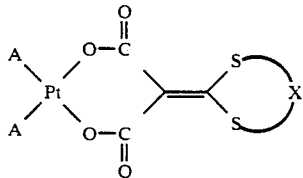

wherein A is selected from the group consisting of ammine and monodentate primary alkyl- and cycloalkylamines having 1-3 carbon atoms such as methyl-, ethyl-, n-propyl-, isopropyl- and cyclopropylamines, or the two amine groups may be combined to form a bidentate diamine of the chelating form $\widehat{AA}$ such as ethylenediamine, 1,2-diaminocyclohexane, and 2-hydroxy-1,3-diaminopropane, and X is either vinylene (—CH=CH—) or ethylene (—$CH_2$—$CH_2$—) when it is bound to two sulfur atoms in a cyclic form or represents two separate methyl groups bound to each sulfur atom.

BACKGROUND OF THE INVENTION

Since the discovery of anti-tumor activity of cisdiamminedichloroplatinum(II) known generically as cisplatin by B. Rosenberg (nature 205, 698(1965)), comprehensive studies including its clinical tests have been performed leading to FDA approval of cisplatin as a chemotherapeutic anti-tumor agent. Currently cisplatin is one of the most widely used anti-tumor agents and in particular, is effective for testicular, ovarian, bladder, head and neck, and lung cancers, but because of its high toxicity ($LD_{50}$=13 mg/Kg), its use is limited. On the other hand, carboplatin, cis-$(NH_3)_2Pt(CBDCA)$(CBDCA=1,1-dicyclobutanedicarboxylate) which was approved by FDA in 1989, has much lower toxicity ($LD_{50}$=180 mg/Kg) compared with cisplatin, but its anti-tumor activity is lower and more expensive than cisplatin. Therefore, a great deal of researches for searching new anti-tumor agents with higher activity and lower toxicity than cisplatin or carboplatin is actively underway.

The exact mechanisms of anti-tumor activity and toxicity of cisplatin are yet to be known, but the recent reviews (Pharmac. Ther. 25, 297-326(1984); Chem. Rev. 87, 1153-1181 (1987)) show that when cisplatin is injected into the blood plasma, it is only partly hydrolyzed and due to the high concentration of chloride ion (~100 mM) in the plasma, its major portion penetrates into the cell as neutral molecule. However, since the chloride concentration in the cell is very low (~4 mM), the majority of the penetrated cisplatin molecules are subjected to hydrolysis with the chloride ligand dissociated, and consequently aquated platinum cations are presumed to combine with DNA in the cell, which prevents replication of DNA leading to killing cells. The platinum complex ions do not distinguish normal cells from tumor cells yielding cytotoxicity, and furthermore, the dimeric and other oligomeric platinum species resultant from the hydrolysis of cisplatin are known to cause severe side effects such as nephrotoxicity.

In spite of a great deal of researches in this field to develop new compounds with higher anti-tumor activity and significantly lower toxicity, no one has been yet successful. The present inventors have now found that some novel platinum complexes chelated by dicarboxylic acid derived from malonic acid as shown in the above formula I are appropriate candidates meeting such criteria.

DETAILED DESCRIPTION OF THE INVENTION

The compounds of this invention is prepared by reaction of diamineplatinum halide with one of the following dicarboxylate ligands, 1,3-dithiol-2-ylidenemalonate (IIa), 1,3-dithiolan-2-ylidenemalonate (IIb), and bis(methylthio)methylenemalonate (IIc), which are represented by the formulae:

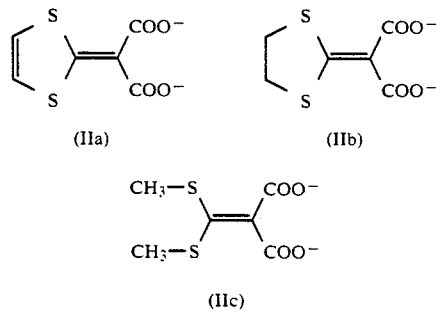

The ethyl or isopropyl esters of these dicarboxylate ligands are easily prepared according to the literature procedure (Acta Chem. Scand. 22, 1107 (1968)) by reaction of ketene mercaptal salt $(K^+S^-)_2CH=CH(COOR)_2$ with vinylidene chloride, dibromoethane or methyliodide. These esters are easily converted to water soluble alkali metal salts by refluxing the esters in the presence of the corresponding alkali metal hydroxide in ethanol solvent. The potassium salt of the dicarboxylate ligands thus prepared may be directly used for the synthesis of the final platinum complexes, or it may be converted to barium salt by reaction with equivalent barium chloride in aqueous solution prior to use for the synthesis of platinum complexes. The potassium or barium salt of the dicarboxylate ligands are reacted with the diamineplatinum sulfate or nitrate to obtain the final platinum complexes depending on the solubility of the final product in aqueous solutions. For instance, if the final platinum complex is only slightly soluble in the aqueous solution, potassium salt of the dicarboxylate ligand is preferred because potassium nitrate or sulfate is soluble in aqueous solution while the platinum complex may precipitate. On the other hand, if the final product is soluble in the aqueous solution, barium salt of the dicarboxylate ligand may better be reacted with diamineplatinum sulfate, because barium sulfate quantitatively precipitates with the platinum complex in the pregnant solution. The pregnant solution may be simply concentrated by evaporation, or organic solvents such as acetone or alcohol may be added to obtain the final product as precipitate.

Diamineplatinum sulfate and nitrate are prepared by reaction of diamineplatinum iodides with silver sulfate and nitrate, respectively, according to the literature procedure (R. C. Harrison, Inorg. Chimica Acta, 46, L15 (1980)), and diamineplatinum iodides are also easily prepared via the literature procedure (M. J. Cleare, Biochimie, 60, 835 (1978)) by adding two equivalent amines per mole of platinum tetraiodide resultant from the reaction of potassium tetrachloride with excess potassium iodide in aqueous solution. Amines suitable for the synthesis of the platinum complexes in this invention include ammonia and monodentate primary alkyl- and cycloalkylamines having 1–3 carbon atoms such as methyl-, ethyl, n-propyl, isopropyl and cyclopropylamine, or the two amine groups may be combined to a bidentate diamine such as ethylenediamine, 1,2-diaminocyclohexane, and 2-hydroxy-1,3-diaminopropane.

The above-mentioned procedure for the preparation of the platinum complexes according to the present invention may be summarized as in the following reaction scheme:

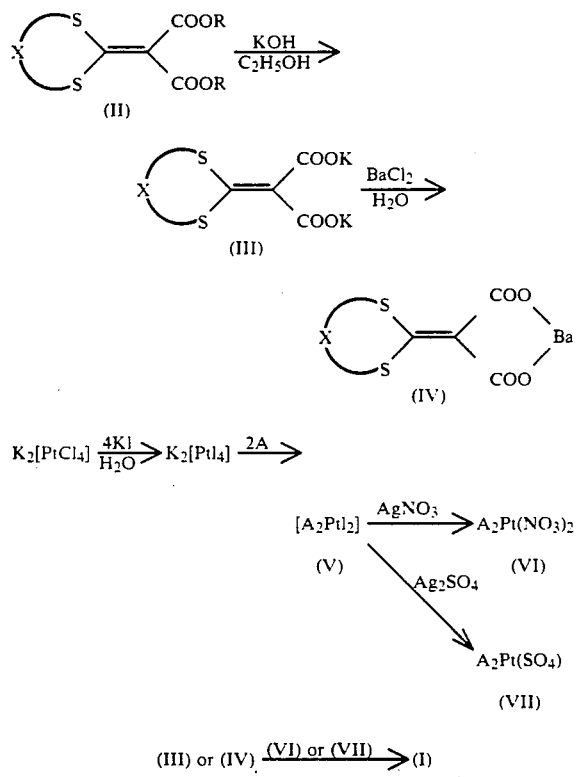

EXAMPLE 1

Preparation of diammine(1,3-dithiol-2-ylidenemalonato) platinum (II)

5.0 g of potassium tetrachloroplatinate and 35 g of potassium iodide were dissolved in 50 ml of deoxygenated distilled water, followed by addition of 1.6 ml of 28% ammonia water, and then the reaction mixture was stirred for hours resulting in a yellow precipitate. The filtered precipitate was washed twice each with distilled water and ethanol and then vacuum dried at room temperature yielding 5.2 g of $(NH_3)_2PtI_2$, which was used as an intermediate for further reactions.

2.11 g of $(NH_3)_2PtI_2$ suspended in 20 ml of distilled water was mixed with 10 ml of aqueous solution containing 1.49 g of silver nitrate and the reaction mixture was stirred for 2 hours. The resultant precipitate of silver iodide was filtered off and the filtrate containing diammineplatinum (II) nitrate was used for reaction with potassium 1,3-dithiol-2-ylidenemalonate obtained as in the following: 6.0 g of diethyl 1,3-dithiol-2-ylidenemalonate or 6.7 g of malotilate, that is, diisopropyl 1,3-dithol-2-ylidenemalonate was refluxed for approximately 5 hours in the presence of 3.3 g of potassium hydroxide in 400 ml of ethanol. The resultant white solid product was filtered, washed three times each with ethanol and ethyl ether, and then vacuum dried at room temperature yielding 4.3 g of potassium 1,3-dithiol-2-ylidenemalonate monoethanolate. 1.44 g of this potassium salt dissolved in 20 ml of distilled water was slowly added to the above diammineplatinum (II) nitrate solution and stirred for approximately 2 hours resulting in a light yellow precipitate. The precipitate was filtered, washed twice each with water and ethanol and then vacuum dried giving 1.02 g (54% yield) of a platinum complex of the following properties:

m.p.: ~140° C. (decomp.)

Elemental analysis (%): C, 15.9; H, 2.25; N, 5.45; S, 15.0. Calculated for $(C_6H_8N_2O_4S_2)Pt(2H_2O)$: C, 15.4; H, 2.59; N, 5.99; S, 13.7.

IR bands(cm$^{-1}$): 673(m), 779(sh), 812(s), 911(m), 1270(sh), 1336(s), 1417(s), 1505(s), 1545(s), 3274(s).

EXAMPLE 2

Preparation of bis(cyclopropylamine)(1,3-dithiol-2-ylidenemalonato)-platinum (II)

Following the procedure of Example 1 and using the same equivalent of cyclopropylamine instead of ammonia, the titled compound was obtained in 50% yield.

m.p.: 130° C. (decomp.)

Elemental analysis(%): C, 26.3; H, 3.58; N, 4.82; S, 12.3; Pt, 33.8.

Calculated for $(C_{12}H_{16}N_2O_4S_2)Pt(2H_2O)$: C, 26.3; H, 3.68; N, 5.12; S, 11.7; Pt, 35.6.

IR bands(cm$^{-1}$): 676(m), 778(m), 817(s), 911(m), 1022(m), 1267(sh), 1336(s), 1410(s), 1457(s), 1548(s), 3094(m), 3198(s).

EXAMPLE 3

Preparation of trans(±)-(1,2-diaminocyclohexane)(1,3-dithiol-2-ylidene-malonato)platinum (II)

Following the procedure of Example 1 and using the same equivalent of trans(±)-1,2-diaminocyclohexane instead of ammonia, the titled compound was obtained in 58% yield.

m.p.: ~180° C. (decomp.)

Elemental analysis(%): C, 25.8; H, 3.22; N, 4.98; S, 12.5; Pt, 32.9. Calculated for $(C_{12}H_{16}N_2O_4S_2)Pt(3H_2O)$: C, 25.5; H, 3.92; N, 4.95; S, 11.3; Pt, 34.5.

IR bands(cm$^{-1}$): 781(m), 817(m), 1267(m), 1333(s), 1418(s), 1484(s), 1561(s), 2861(m), 2937(m), 3064(s), 3212(s).

EXAMPLE 4

Preparation of trans(1R,2R)-(1,2-diaminocyclohexane)(1,3-dithiol-2-ylidenemalonato)platinum (II)

Following the procedure of Example 1 and using the same equivalent of trans(1R, 2R)-1,2-diaminocyclohexane instead of ammonia, the titled compound was obtained in 55% yield.

m.p.: ~197° C. (decomp.)

Elemental analysis(%): C, 26.0; H, 3.42; N, 5.17; S, 11.6; Pt, 35.2. Calculated for $(C_{12}H_{16}N_2O_4S_2)Pt(2H_2O)$: C, 26.3; H, 3.66; N, 5.12; S, 11.7; Pt, 35.6.

IR bands(cm$^{-1}$): 676(m), 815(m), 1030(m), 1066(m), 1174(m), 1267(m), 1333(s), 1418(s), 1508(s), 1556(s), 2861(m), 2939(m), 3064(s), 3212(s).

EXAMPLE 5

Preparation of bis(isopropylamine)(1,3-dithiol-2-ylidenemalonato)-platinum(II)

Following the procedure of Example 1 and using the same equivalent of iso-propylamine instead of ammonia, the titled compound was obtained in 46% yield.

m.p.: ~135° C. (decomp.)

Elemental analysis(%): C, 28.2; H, 3.13; N, 5.48. Calculated for $(C_{12}H_{20}N_2O_4S_2)Pt$: C, 28.0; H, 3.91; N, 5.43.

IR bands(cm$^{-1}$): 663(m), 784(m), 816(m), 1116(m), 1158(m), 1269(m), 1329(s), 1422(s), 1459(sh), 1502(sh), 1545(sh), 2973(m), 3114(m), 3214(m).

EXAMPLE 6

Preparation of ethylenediamine(1,3-dithiol-2-ylidenemalonato)-platinum(II)

Following the procedure of Example 1 and using the same equivalent of ethylenediamine instead of ammonia, the titled compound was obtained in 64% yield.

m.p.: ~193° C. (decomp.)

Elemental analysis(%): C, 19.6; H, 2.73; N, 5.46; S, 13.3; Pt, 38.5. Calculated for $(C_8H_{10}N_2O_4S_2)\cdot Pt(2H_2O)$: C, 19.5; H, 2.83; N, 5.67; S, 13.0; Pt, 39.5.

IR bands(cm$^{-1}$): 673(m), 767(m), 916(m), 1057(m), 1198(m), 1139(s), 1412(s), 1539(s), 1605(m), 3133(m), 3240(m).

EXAMPLE 7

Preparation of (2-hydroxy-1,3-diaminopropane)(1,3-dithiol-2-ylidenemalonato)platinum(II)

2.4 g of potassium 1,3-dithiol-2-ylidenemalonate prepared in Example 1 is dissolved in 300 ml of distilled water and mixed with 200 ml of aqueous solution containing 1.95 g of $BaCl_2 \cdot 2H_2O$. The resultant white precipitate was filtered, washed twice each with water and ethanol, and then vacuum dried yielding 2.15 g of barium 1,3-dithiol-2-ylidenemalonate monohydrate (81% yield), which was used for reaction with the amine-platinum sulfate solution prepared as in the following.

1.06 g of 2-hydroxy-1,3-diaminopropaneplatinum (II) iodide prepared following the procedure of Example 1 using 2-hydroxy-1,3-diaminopropane instead of ammonia was suspended in 100 ml of distilled water and reacted with 0.612 g of silver sulfate for 4 hours. The precipitate of silver iodide was filtered off, and the filtrate containing 2-hydroxy-1,3-diaminopropane-platinum (II) sulfate was added to a suspension of 0.70 g of barium 1,3-dithiol-2-ylidenemalonate in 100 ml of distilled water. After the reaction mixture was stirred for 2 hours, the white precipitate of barium sulfate was filtered off and the filtrate was concentrated to 20 ml by evaporation. 30 ml of acetone was added to the concentrate resulting in a light yellow precipitate. The filtered precipitate was washed twice each with acetone and ethylether and then vacuum dried at room temperature. 0.69 g (72% yield) of titled compound was obtained.

m.p.: ~170° C. (decomp.)

Elemental analysis(%): C, 20.9; H, 2.71; N, 5.28; S, 12.8; Pt, 36.9. Calculated for $(C_9H_{12}N_2O_5S_2)Pt(2H_2O)$: C, 20.7; H, 2.31; N, 5.35; S, 12.2; Pt, 37.3.

IR bands(cm$^{-1}$): 677(m), 797(m), 912(m), 1034(m), 1086(m), 1360(s), 1543(s), 2946(sh), 3125(sh), 3216(s).

EXAMPLE 8

Preparation of diammine(1,3-dithiolan-2-ylidenemalonato)platinum(II)

Following the procedure of Example 1 and using diethyl 1,3-dithiolan-2-ylidenemalonate instead of diethyl 1,3-dithiol-2-ylidenemalonate, potassium 1,3-dithiolan-2-ylidenemalonate monoethanolate was obtained, and then converted to barium 1,3-dithiolan-2-ylidenemalonate dihydrate using the same procedure of Example 7. 1.32 g of this barium salt suspended in 100 ml of distilled water was reacted for 2 hours with an aqueous solution of diammineplatinum(II) sulfate prepared by reaction of 1.45 g of diammineplatinum(II) iodide and 0.933 g of silver sulfate in 300 ml of distilled water also following the same procedure of Example 7. The resultant precipitate of barium sulfate was filtered off and the filtrate was concentrated to approximately 10 ml. 20 ml of ethanol was added to this concentrate yielding a yellow precipitate, which was filtered, washed twice each with ethanol and ethyleter and then vacuum dried. 0.78 g (60% yield) of titled compound was obtained.

m.p.: ~180° C. (decomp.)

Elemental analysis(%): C, 13.8; H, 2.49; N, 6.11; S, 12.3; Pt, 40.7. Calculated for $(C_6H_{10}N_2O_4S_2)Pt(4H_2O)$: C, 14.2; H, 3.56; N, 5.54; S, 12.7; Pt, 38.6.

IR bands(cm$^{-1}$): 819(m), 1105(m), 1249(sh), 1338(s), 1440(sh), 1584(s), 3250(s), 3410(m).

EXAMPLE 9

Preparation of bis(cyclopropylamine)(1,3-dithiolan-2-ylidenemalonato)platinum(II)

Following the procedure of Example 1 and using cyclopropylamine instead of ammonia, bis(cyclopropylamine)platinum(II) iodide was obtained and then converted to water soluble bis(cyclopropylamine) platinum(II) sulfate, which was reacted with barium 1,3-dithiolan-2-ylidenemalonate according to the same procedure of Example 8. After the precipitate of barium sulfate was filtered off, the filtrate was concentrated to approximately 10 ml, and then 20 ml ethanol and 30 ml of ethylether were added. The resultant precipitate was filtered, washed twice each with ethanol and ethylether and then vacuum dried. The titled compound was obtained in 41% yield.

m.p.: ~170° C. (decomp.)

Elemental analysis(%): C, 24.6; H, 3.32; N, 4.45; Pt, 34.7. Calculated for $(C_{12}H_{18}N_2O_4S_2)Pt(4H_2O)$: C, 24.6; H, 4.48; N, 4.78; Pt. 33.3.

IR bands(cm$^{-1}$): 799(m), 817(m), 1021(m), 1100(m), 1261(m), 1280(m), 1336(s), 1422(m), 1458(m), 1593(m), 3106(m), 3205(m), 3420(m).

EXAMPLE 10

Preparation of
trans(±)-(1,2-diaminocyclohexane)(1,3-dithiolan-2-ylidenemalonato)platinum(II)

Following the procedure of Example 9 and using the same equivalent of trans-(±)-1,2-diaminocyclohexane instead of cyclopropylamine, the title compound was obtained in 64% yield.

m.p.: ~200° C. (decomp.)

Elemental analysis(%): C, 25.8; H, 3.80; N, 5.07; S, 12.4; Pt, 35.8. Calculated for $(C_{12}H_{18}N_2O_4S_2)Pt(2H_2O)$: C, 26.2; H, 4.03; N, 5.10; S, 11.7; Pt, 35.5.

IR bands(cm$^{-1}$): 743(m), 819(m), 1030(m), 1062(m), 1123(m), 1156(m), 1249(sh), 1280(sh), 1342(s), 1446(m), 1577(s), 2933(m), 3214(m), 3396(m).

EXAMPLE 11

Preparation of
ethylenediamine(1,3-dithiolan-2-ylidenemalonato)-platinum(II)

Following the procedure of Example 1 and using the same equivalent of ethylenediamine instead of ammonia, ethylenediamineplatinum(II) iodide was obtained and then converted to water soluble ethylenediamineplatinum(II) sulfate, which was reacted with barium 1,3-dithiolan-2-ylidenemalonate according to the same procedure of Example 8. After the precipitate of barium sulfate was filtered off, the filtrate was concentrated to approximately 10 ml by vacuum evaporation and then 50 ml of acetone was added. The resultant precipitate was filtered, washed twice each with acetone and ethylether, and vacuum dried. The titled compound was obtained in 45% yield.

m.p.: ~175° C. (decomp.)

Elemental analysis(%): C, 20.3; H, 3.07; N, 5.39. Calculated for $(C_8H_{12}N_2O_4S_2)Pt(H_2O)$: C, 20.1; H, 2.96; N, 5.87.

IR bands(cm$^{-1}$): 773(m), 822(m), 887(sh), 1053(m), 1154(m), 1280(sh), 1329(s), 1454(s), 1591(s), 3111(s), 3212(s), 3420(s).

EXAMPLE 12

Preparation of
(2-hydroxy-1,3-diaminopropane)(1,3-dithiolan-2-ylidenemalonato)planium(II)

Following the procedure of Example 11 and using the same equivalent of 2-hydroxy-1,3-diaminopropane instead of ethylenediamine, the titled compound was obtained in 62% yield.

m.p.: ~205° C. (decomp.)

Elemental analysis(%): C, 20.5; H, 2.83; N, 5.33; S, 12.7. Calculated for $(C_9H_{14}N_2O_5S_2)Pt(2H_2O)$: C, 20.6; H, 2.69; N, 5.33; S, 12.2.

IR bands(cm$^{-1}$): 721(m), 804(m), 882(m), 1040(m), 1207(m), 1283(sh), 1360(s), 1462(m), 1589(s), 3235(s), 3374(s), 3495(s).

EXAMPLE 13

Preparation of
diammine[bis(methylthio)methylenemalonato]platinum(II)

Following the procedure of Example 1 and using 6.9 g of diethyl bis(methylthio)methylenemalonate instead of diethyl 1,3-dithiol-2-ylidenemalonate was obtained 6.9 g of potassium bis(methylthio)methylenemanonate monohydrate which was then reacted with 5.59 g of barium chloride dihydrate following the procedure of Example 7. The resultant aqueous reaction mixture was concentrated to approximately 20 ml by evaporation yielding white crystalline product, which was filtered, washed twice each with ethanol and ethylether and vacuum dried. 6.0 g of barium bis(methylthio)methylenemalonate dihydrate was obtained. Following the procedure of Example 7 and using 1.0 of this barium salt and 1.27 g of diammineplatinum(II) iodide, 1.01 g (88% yield) of the titled compound was obtained.

m.p.: ~158° C. (decomp.)

Elemental analysis(%): C, 16.5; H, 3.02; N, 5.61; S, 13.1; Pt, 42.9. Calculated for $(C_6H_{12}N_2O_4S_2)Pt(H_2O)$: C, 15.9; H, 3.09; N, 6.18; S, 14.1; Pt, 43.0.

IR bands(cm$^{-1}$): 724(m), 977(m), 1094(m), 1325(s), 1373(s), 1626(s), 3159(s), 3398(s).

EXAMPLE 14

Preparation of
[bis(cyclopropylamine)][bis(methylthio)methylene malonato]platinum(II)

Following the procedure of Example 13 and using the same equivalent of bis(cyclopropylamine)platinum-(II) iodide instead of diammineplatinum (II) iodide, the titled compound was obtained in 72% yield.

m.p.: ~155° C. (decomp.)

Elemental analysis(%): C, 25.3; H, 3.69; N, 4.72; S, 11.9. Calculated for $(C_{12}H_{20}N_2O_4S_2)Pt(3H_2O)$: C, 25.3; H, 4.60; N, 4.92; S, 11.3.

IR bands(cm$^{-1}$): 725(m), 824(m), 974(m), 1026(m), 1319(s), 1363(s), 1459(sh), 1621(s), 3016(s), 3200(s), 3451(s).

EXAMPLE 15

Preparation of
trans(±)-(1,2-diaminocyclohexane)[bis(methylthio)methylenemalonato]platinum(II)

Following the procedure of Example 13 and using the same equivalent of trans(±)-(1,2-diaminocyclohexamen)platinum(II) iodide instead of diammineplatinum-(II) iodide, the titled compound was obtained in 75% yield.

m.p.: ~175° C. (decomp.)

Elemental analysis(%): C, 25.6; H, 4.18; N, 4.98; Pt, 35.8. Calculated for $(C_{12}H_{20}N_2O_4S_2)Pt(3H_2O)$: C, 25.3; H, 4.60; N, 4.92; Pt, 34.3.

IR bands(cm$^{-1}$): 604(m), 729(m), 978(m), 1031(m), 1064(m), 1177(m), 1328(s), 1373(s), 1607(s), 2938(s), 3010(s), 3400(s).

EXAMPLE 16

Preparation of
ethylenediamine[bis(methylthio)methylenemalonato]-platinum(II)

Following the procedure of Example 13 and using the same equivalent of ethylenediamineplatinum(II) iodide instead of diammineplatinum(II) iodide, the titled compound was obtained in 74% yield.

m.p.: ~115° C. (decomp.)

Elemental analysis(%): C, 17.0; H, 3.34; N, 5.58; S, 11.5. Calculated for $(C_8H_{14}N_2O_4S_2)Pt(5H_2O)$: C, 17.3; H, 3.64; N, 5.06; S, 11.6.

IR bands(cm$^{-1}$): 619(m), 748(m), 982(m), 1053(m), 1123(m), 1333(s), 1372(sh), 1582(s), 3075(s), 3200(s), 3420(s).

EXAMPLE 17

Preparation of (2-hydroxy-1,3-diaminopropane)[bis(methylthio)methylenemalonato]platinum(II)

Following the procedure of Example 13 and using the same equivalent of (2-hydroxy-1,3-diaminopropane)platinum(II) iodide instead of diammineplatinum(II) iodide, the title compound was obtained in 89% yield.

m.p.: ~168° C. (decomp.)

Elemental analysis(%): C, 20.2; H, 3.54; N, 5.19; S, 13.5; Pt, 38.0. Calculated for $(C_9H_{16}N_2O_5S_2)Pt(2H_2O)$: C, 20.5; H, 3.79; N, 5.31; S, 12.2; Pt, 37.0.

IR bands(cm$^{-1}$): 642(m), 729(m), 972(m), 1086(m), 1321(m), 1373(s), 1453(sh), 1609(s), 3173(s), 3437(s).

In vivo test against leukemia L1210 cell ine

Each test group consisted of 8 BDF1 mice of 6 to 8 weeks old. 10$^6$ cells of leukemia L1210 were implanted by intraperitoneal injection to each animal, and the platinum test compounds dissolved in physiological saline solution were administered intraperitoneally on days 1, 5 and 9 at various doses in the range of 1–20 mg/Kg. Test results are illustrated in the following table.

| Compounds | Doses, mg/Kg | Increase in Life Span (ILS), % | Number of survived animals |
|---|---|---|---|
| Example 2 | 4 | >138 | 4/8 |
|  | 0.8 | 35 | 2/8 |
| Example 3 | 4 | 43 | 0 |
|  | 1 | 16 | 0 |
| Example 9 | 4 | 129 | 3/8 |
|  | 1 | 27 | 0 |
| Example 14 | 10 | 41 | 0 |
|  | 4 | 20 | 0 |
| cisplatin | 4 | 64 | 0 |
|  | 0.8 | 6 | 0 |
| carboplatin | 20 | 28 | 0 |

What is claimed is:

1. A platinum complex of the general formula:

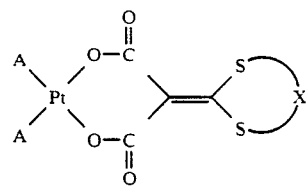

wherein X is —CH$_2$—CH$_2$—, or —CH=CH— when it is bound to two sulfur atoms in a cyclic form, or X represents two methyl groups separately bound to each sulfur atom, and A is selected from the group consisting of ammonia, methylamine, ethylamine, isopropylamine and cyclopropylamine, or the two amine groups may be combined together to form ethylenediamine, 1,2-diaminocyclohexane, or 2-hydroxy-1,3-diaminopropane.

2. A process for preparing the platinum complex as set forth in claim 1 comprising reacting the diamineplatinum(II) nitrate, $A_2Pt(NO_3)_2$ with equimolar potassium salt of the formula,

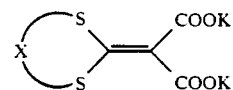

in aqueous solution at room temperature, wherein A and X are the same as in claim 1.

3. A process for preparing the platinum complex as set forth in claim 1 comprising reacting the daimineplatinum(II) sulfate, $A_2Pt(SO_4)$ with equimolar barium salt of the formula,

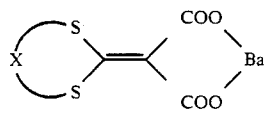

in aqueous solution at room temperature and then adding the organic solvents to the filtrate concentrated, wherein A and X are the same as in claim 1.

4. A process according to claim 3, wherein the organic solvent is selected from the group consisting of acetone, ethanol and ethylether.

* * * * *

UNITED STATES PATENT AND TRADEMARK OFFICE
CERTIFICATE OF CORRECTION

PATENT NO. : 5,142,075
DATED : August 25, 1992
INVENTOR(S) : Youn Soo Sohn, et al.

It is certified that error appears in the above-indentified patent and that said Letters Patent is hereby corrected as shown below:

Column 8, line 8, "1.0" should read --1.0 g--.

Signed and Sealed this

Thirtieth Day of November, 1993

Attest:

BRUCE LEHMAN

Attesting Officer    Commissioner of Patents and Trademarks